United States Patent [19]

Damó et al.

[11] Patent Number: 5,154,754
[45] Date of Patent: Oct. 13, 1992

[54] OIL-IN-WATER EMULSIONS AND A PROCESS FOR THEIR PREPARATION AND THEIR USE

[75] Inventors: Zoltan Damó, Eppstein/Taunus; Gerhard Frisch, Wehrheim; Hans Röchling, Bad Soden am Taunus; Heinz-Josef Niessen, Bergisch-Gladbach; Wolfgang Wirth, Hennef, all of Fed. Rep. of Germany

[73] Assignee: Hoechst Aktiengesellschaft, Frankfurt am Main, Fed. Rep. of Germany

[21] Appl. No.: 517,451

[22] Filed: May 2, 1990

Related U.S. Application Data

[63] Continuation of Ser. No. 166,036, Mar. 9, 1988, abandoned.

[30] Foreign Application Priority Data

Mar. 11, 1987 [DE] Fed. Rep. of Germany ....... 3707711

[51] Int. Cl.$^5$ .................... A01N 25/30; A01N 57/02; C07C 43/11; C07C 309/01
[52] U.S. Cl. ........................................... 71/79; 71/86; 71/DIG. 1; 252/312; 514/147; 558/210; 562/36; 562/89; 562/91; 568/606; 568/609; 568/644
[58] Field of Search ...................... 252/312; 558/210; 514/147; 71/DIG. 1

[56] References Cited

U.S. PATENT DOCUMENTS

| | | | |
|---|---|---|---|
| 2,898,267 | 8/1959 | Lindner | 167/42 |
| 4,107,302 | 8/1978 | Watanabe | 424/200 |
| 4,303,640 | 12/1981 | Fuyama et al. | 424/78 |
| 4,500,348 | 2/1985 | Hausmann et al. | 71/103 |
| 4,564,632 | 1/1986 | Nonn et al. | 514/522 |
| 4,681,900 | 7/1987 | Iwasaki | 514/786 |
| 4,731,378 | 3/1988 | Naik et al. | 514/531 |
| 4,824,663 | 4/1989 | Wirth et al. | 424/78 |

FOREIGN PATENT DOCUMENTS

| | | |
|---|---|---|
| 1209361 | 8/1986 | Canada . |
| 1209362 | 8/1986 | Canada . |
| 0160182 | 11/1985 | European Pat. Off. . |
| 2041480 | 10/1973 | Fed. Rep. of Germany . |
| 854952 | 11/1960 | United Kingdom . |

*Primary Examiner*—Richard L. Raymond
*Assistant Examiner*—S. Mark Clardy

[57] ABSTRACT

Oil-in-water emulsions (microemulsions) containing 0.01–80% by weight of at least one agrochemical active substance of low water-solubility, one active substance for combating pests in the domestic and hygiene sector and/or one pharmacologically active substance, 1% to 30% by weight of an emulsifier mixture of non, ionic and anionic compounds and at least one alkylarylsulfonic acid salt, as defined in the description, as well as water and, if appropriate, 1% to 30% by weight of at least one solvent of low water-miscibility and/or one solubilizer, and if appropriate 0.05% to 15% by weight of additives, the sum of the components in each case being 100% by weight, a process for the preparation of these aqueous microemulsions and their use.

10 Claims, No Drawings

OIL-IN-WATER EMULSIONS AND A PROCESS FOR THEIR PREPARATION AND THEIR USE

This is a continuation of Ser. No. 07/166,036, filed 03/09/88, now abandoned.

The present invention relates to oil-in-water emulsions, specifically an oil-in-water microemulsion of agrochemical active substances, active substances for combating pests in the domestic and hygiene sector and/or pharmacologically active substances. The invention also relates to a process for the preparation of these oil-in-water emulsions and their use.

Oil-in-water emulsions of numerous agrochemical active substances of low water-solubility which each also contain, in addition to the active substances, a surface-active substance and a thickening agent or a relatively large amount of surface-active substances are already known (compare U.S. Pat. No. 4,303,640, DE-A 30 11 611, FR-A 2 452 250 and JP-A 122 628-77). This addition of thickening agent or of large amounts of surfactant is associated with additional costs and thus represents a serious disadvantage of the known oil-in-water emulsions. Furthermore, the preparation previously described for such emulsions is not generally applicable. In particular, essentially only those active substances which have a low water-solubility and are liquid at room temperature or at least have a very low melting point can be emulsified by this process.

It is also a disadvantage that the known oil-in-water emulsions often are not sufficiently stable at low temperatures, and that in some cases force emulsification with the aid of homogenizers is necessary.

Numerous alkylaryl polyglycol ethers and their use as emulsifiers in agrochemical agents are furthermore known from DE-C 824 949, GB 85 4952, CH-A 275 705 and U.S. Pat. No. 4,564,632. Combinations of these nonionic emulsifiers with ionic components, however, are not mentioned in the publications referred to. DE-A 2 041 480 furthermore shows that emulsifier combinations of an ionic and a non-ionic component are suitable for the preparation of emulsions containing agrochemical active substances. However, the emulsions in question contain relatively large amounts of organic solvents and are stable for only a relatively short time.

Improved homogeneous aqueous formulations with alkylaryl polyglycol ethers as emulsifiers are also described in U.S. Pat. No. 4,500,348, CA 1,209,361 and CA 1,209,362.

Oil-in-water emulsions (microemulsions) which contain 0.01–80% by weight of at least one agrochemical active substance of low water-solubility, of an active substance for combating pests in the domestic and hygiene sectors and/or of a pharmacologically active substance, 1 to 30% by weight of an emulsifier mixture of a) 30–80, preferably 50–60% by weight of one or more compounds of the formulae I–V

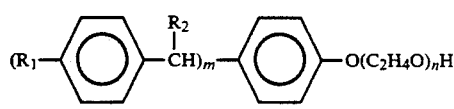

in which
R$_1$ denotes hydrogen or C$_1$–C$_{16}$-alkyl,
R$_2$ denotes hydrogen or methyl,
m denotes a number from 1 to 4 and
n denotes a number from 10 to 60,

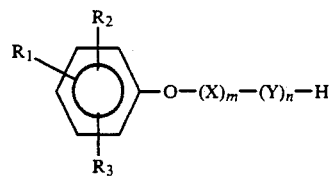

in which
R$_1$, R$_2$ and R$_3$ each denote hydrogen or C$_1$–C$_{20}$-alkyl,
X and Y denote an oxyethylene or oxypropylene group, but X and Y do not simultaneously represent an oxyethylene or oxypropylene unit,
m denotes a number from 2 to 45 and
n denotes a number from 2 to 90,

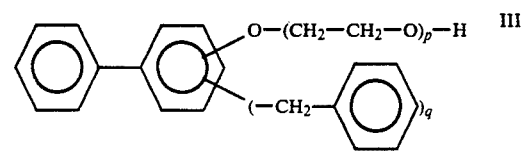

in which
p denotes a number from 5–40 and
q denotes a number from 1–3,

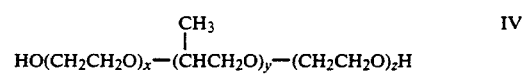

in which x, y and z represent numbers which are chosen so that the molecular weight is 1,800 to 16,000 in total,

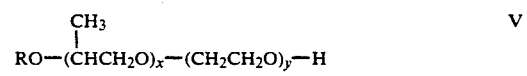

in which R denotes C$_3$–C$_{18}$-alkyl and x and y represent numbers which are chosen so that the molecular weight is 2,000 to 7,000 in total, b) 20–50, preferably 30–40% by weight of a compound of the formula VI

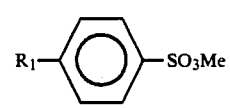

in which R$_1$ denotes C$_4$–C$_{35}$-alkyl and Me denotes a metal cation from group II or III of the periodic table, and c) 0.1–20, preferably 0.1–10% by weight of one or more compounds of the formulae VII–XIII

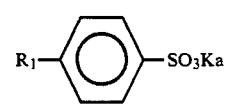

in which R$_1$ has the same meaning as for formula VI and Ka denotes a cation, excluding the cations with the meaning under Me in formula VI, RO—(CH₂CH₂O)ₓSO₃Ka    VIII in which R denotes C₆-C₁₈-alkyl, x denotes a number from 2 to 8 and Ka has the meaning given in the case of formula VII,

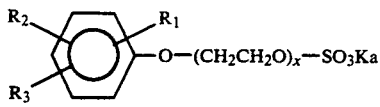
IX in which R₁, R₂ and R₃ denotes hydrogen or C₁-C₂₀-alkyl, x denotes a number from 5 to 50 and Ka has the meaning given in the case of formula VII, R—(O)ₙSO₃Ka    X in which R denotes C₈-C₁₈-alkyl or C₈-C₁₈-alkenyl or, in the case where n=0, also denotes C₄-C₁₈-chloroalkyl, n denotes 0 or 1 and Ka has the meaning given in the case of formula VII,

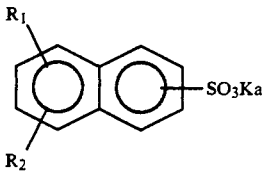
XI in which R₁ denotes C₃-C₁₃-alkyl and R₂ denotes hydrogen, or R₁ and R₂ denote C₃-C₁₃-alkyl and Ka has the meaning given in the case of formula VII, R—SO₂—N—A—COOKa    XII
         |
         R₁ in which
R denotes C₁₂-C₂₄-alkyl, phenyl, naphthyl or anthracinyl,
R₁ denotes hydrogen or C₁-C₄-alkyl and A denotes an alkylene radical which has more than 4 carbon atoms and is optionally substituted by one or more methyl or ethyl groups, and Ka has the meanings given in the case of formula VII, R—CON—(CH₂)ₘ—COOKa    XIII
     |
     R₁ in which
R denotes C₁₂-C₁₈-alkyl or C₆-C₁₄-cycloalkyl,
R₁ denotes hydrogen or C₁-C₆-alkyl, m denotes 1 or 2 and Ka has the meanings given in the case of formula VII,
and water, and
if appropriate 1 to 30% by weight of at least one organic solvent of low water-miscibility and/or of one stabilizer and
if appropriate 0.1 to 15% by weight of additives, the sum of the components in each case being 100% by weight, have now been found.

It is extremely surprising that the oil-in-water emulsions (microemulsions) according to the invention are not only stable under conditions such as are described, inter alia, in EP-A 0 062 181, EP-A 0 107 009 and EP-A 0 107 023, but are also both chemically and physically stable above 35° C. and below +10° C. to −10° C. for up to 3 months or more. The outstanding resistance to high temperatures and stability to low temperatures of the emulsions according to the invention could not be predicted.

Taking into consideration the technical doctrine from DE-A 2 041 480, it furthermore had to be assumed that emulsifier combinations of an ionic and a nonionic component are also only suitable for the preparation of stable aqueous emulsions if a relatively large amount of organic solvents is present. In contrast to expectations, it has been found that the microemulsions according to the invention are distinguished by an outstanding stability also at high temperatures, although they contain only small amounts of organic solvents, if any. Even when they contain relatively large amounts of solvents, microemulsions which have a particularly high thermodynamic stability and are not the usual oil-in-water emulsions still result. A good stability to low temperatures is also guaranteed.

The oil-in-water emulsions (microemulsions) according to the invention are distinguished by a number of advantages:
small amounts of organic solvents, if any,
high flashpoint of the emulsions,
no odor nuisance form organic solvents,
lower phytotoxicity in comparison with the conventional formulations,
both physically and chemically stable under conditions in practice,
on long-term storage, these emulsions remain chemically and physically unchanged between −10° C. and +54° C.,
easy preparation of the emulsions (no homogenizers necessary), merely by stirring,
active substances which are solid or liquid at room temperature and of low water-solubility can equally well be emulsified to microemulsions.

The emulsions according to the invention are microemulsions, and contain at least one agrochemical active substance of low water-solubility, an active substance for combating pests in the domestic and hygiene sector and/or a pharmacologically active substance. These active substances are in the liquid or dissolved state in the oil phase.

Possible active substances are both those substances which are liquid at room temperature and those which are solid at room temperature. A condition for liquid active substances is merely that they are sparingly soluble in water. The solubility of these substances in water at 20° C. is not more than 0.5% by weight. Solid active substances, however, must furthermore be sufficiently soluble in an organic solvent of low water-miscibility and/or a solubilizer.

Agrochemical substances in the present case are to be understood as all the active substances usually employed in plant protection. These include, for example, insecticides, arcaricides, nematicides, fungicides, herbicides, growth regulators and fertilizers. Specific examples of such active substances which may be mentioned are:
ethyl 2-diethoxythiophosphoryloxy-5-methyl-pyrazolo [1,5-a]pyrimidine-6-carboxylate
methyl 2-[4,(2,4-dichlorophenoxy)phenoxy]propionate
7-chlorobicyclo[3.2.0]-hepta-2,6-dien-6-yl dimethyl phosphate O,O-diethyl O-1-phenyl-1,2,4-triazol-3-yl phosphorothoate
1,4,5,6,7,7-hexachloro-8,9,10-trinorborn-5-en-2,3-ylene dimethyl sulfite
(S)-α-cyano-3-phenoxybenzyl (1R, 3R)-3-(2,2-diromovinyl)-2,2-dimethylcyclopropanecarboxylate
butylglycol (4-chloro-o-tolyloxy)acetate
butylglycol 2-(4-chloro-o-tolyloxy)propionate
α,α,α-trifluoro-2,6-dinitro-N,N-dipropyl-p-toluidine
O,O-diethyl O-(4-nitro-phenyl) thiono-phosphate
O,O-dimethyl O-(4-nitro-phenyl) thiono-phosphate
O-ethyl O-(4-methylthio-phenyl) S-propyl dithiophosphate
O,O-(diethylthionophosphoryl)-α-oximino-phenylacetonitrile
ethyl ±2-[4-(6-chlorobenzoxazol-2-yloxy)phenoxy]-propionate
2-isopropoxy-phenyl N-methylcarbamate
3-methylthio-4-amino-6-ter.-butyl-1,2,4-triazin-5-one
3-methylthio-4-isobutylideneamino-6-tert.-butyl-1,2,4-triazin-5-one
2-chloro-4-ethylamino-6-isopropylamino-1,3,5-triazine
2,3-dihydro-2,2-dimethyl-7-benzofuranyl methyl-carbamate
3,5-dimethyl-4-methylthiophenyl N-methyl-carbamate
O,O-diethyl O-(3-chloro-4-methyl-7-coumarinyl) thiophosphate
γ-hexachlorocyclohexane
6,7,8,9,10,10-hexachloro-1,5,5A,6,9,9A-hexahydro-6,9-methane-2,4,3-benzo-dioxathiepine 3-oxide
1,4,5,6,7,8,8,-heptachloro-4,7-endo-methylene-3A,4,7-,7A-tetrahydroindene
2-(2-furyl)-benzimidazole
5-amino-1-bis-(dimethylamido)-phosphoryl-3-phenyl-1,2,4-triazole
4-hydroxy-3-(1,2,3,4-tetrahydro-1-naphthyl)-coumarin
S-[1,2-bis-(ethoxycarbonyl)-ethyl] O,O-dimethyl dithiophosphate
O,O-dimethyl O-(4-methylmercapto-3-methyl-phenyl) thionophosphate
O-ethyl O-(2-isopropyloxycarbonyl-phenyl) N-isopropylthionophosphoramide
1-(4-chlorophenoxy)-3,3-dimethyl-1-(1,2,4-triazol-1-yl)-2-butanone
(S)-α-cyano-3-phenoxybenzyl (1R)-cis-3-(2,2-dibromovinyl)-2,2-dimethylcyclo-propanecarboxylate
α-cyano-3-phenoxy-4-fluoro-benzyl 2,2-dimethyl-3-(β,β dichlorovinyl)-cyclopropanecarboxylate.

Active substances for combating pests in the domestic and hydgiene sector are to be understood, in the present case, as all the usual active substances of low water-solubility. Specific examples of such active substances which may be mentioned are:
2-isopropoxy-phenyl N-methylcarbamate
O,O-diethyl O-(4-nitro-phenyl) thionophosphate
O,O-dimethyl O-(4-nitro-phenyl) thionophosphate
S-[1,2-bis-(ethoxycarbonyl)-ethyl] O,O-dimethyl dithiophosphate
O,O-dimethyl O-(3-methyl-4-nitro-phenyl) thionophosphate
O,O-dimethyl O-(4-methylmercapto-3-methyl-phenyl) thionophosphate
γ-hexachlorocyclohexane
cyclohex-1-ene-1,2-dicarboximidomethyl 2,2-dimethyl-3-(2-methylpropenyl)-cyclopropanecarboxylate.

Pharmacologically active substances in the present case are preferably to be understood as substances which can be used in the veterinary medicine field and are of low water-solubility. An example of such active substances which may be mentioned are:
γ-cyano-3-phenoxy-4-fluoro-benzyl 2,2-dimethyl-3-[β-(p-chlorophenyl)-β-chlorovinyl]-cyclopropanecarboxylate The nionionic compounds contained as emulsifiers in the oil-in-water emulsions (microemulsions) according to the invention are defined under the formulae I-V.

Specific examples of alkylaryl polyglycol ethers of the formula I which may be mentioned are:
bis-]α-methyl-(4-methyl-benzyl)]-phenyl polyglycol ether with on average 27 mol of ethylene oxide units per molecule.
bis-]α-methyl(4-dodecyl-benzyl)]-phenyl polyglycol ether with on average 27 mol of ethylene oxide units per molecule.
tris-[α-methyl(4-methyl-benzyl)]-phenyl polyglycol ether with on average 17 mol of ethylene oxide units per molecule.
tris-(α-methyl-benzyl)-phenyl polyglycol ether with on average 22 mol of ethylene oxide units per molecule.
tris-(α-methyl-benzyl)-phenyl polyglycol ether with on average 40 mol of ethylene oxide units per molecule.

The emulsifiers of this type used in practice are in general mixtures of several compounds of the formula I which differ by the degree of substitution on the phenyl ring. Fractions are therefore also calculated as mean values of the index n (formula I). Substances as described under formula I for which the following average compositions result may be mentioned as examples:

| | | |
|---|---|---|
| $R_1 = H$; | $m = 2.7$; | $n = 22$ |
| $R_1 = CH_3$; | $m = 2.7$; | $n = 27$ |
| $R_1 = H$; | $m = 2.7$; | $n = 40$ |

The alkylaryl polyglycol ethers of the formula I are known.

In the alkylaryl polyglycol ethers of the formula II, $R_1$, $R_2$ and $R_3$ preferably stand for $C_1-C_4$-alkyl or $R_1$ alternating with $R_2$ and $R_3$ stand for $C_1-C_{20}$-alkyl and $R_2$ with $R_3$ stand for hydrogen atoms. X and Y each stand for an oxyethylene or oxypropylene group, but X and Y do not simultaneously stand for an oxyethylene or oxypropylene unit. The index m preferably stands for numbers from 10 to 30 and the index n preferably stands for numbers from 10 to 40. The numbers for the indices m and n represent average values.

The emulsifiers of this type used in practice are in general mixtures of several compounds of the formula II. In particular, they are mixtures of compounds which differ on the one hand by the number of ethylene oxide or propylene oxide units and on the other hand by the nature of the alkyl substituents. Examples which may be mentioned are substances for which the following average compositions result:

II a $R_1$=butyl; $R_2$=butyl; $R_3$=butyl; X=prpylene oxide; Y=ethylene oxide; m=10 mol; n=30 mol;
II b $R_1$=nonyl; $R_2$=H; $R_3$=H; X=propylene oxide; Y=ethylene oxide; m=24 mol; n=40 mol The alkylaryl polyglycol ethers of the formula II are known.

In the aryl polyglycol ethers of the formula III, the index p preferably stands for numbers from 8 to 18 and the index q preferably stands for numbers from 1 to 2.

The numbers for the indices p and q represent average values.

The emulsifiers of this type which are used in practice are in general mixtures of several compounds of the formula III. In particular, they are mixtures of compounds which differ by the number of ethylene oxide units and by the degree of substitution on the phenyl radical. Fractions can thereby also be calculated as mean values for the indices p and q. Substances for which the following average compositions result may be mentioned as examples:

IIIa p=11; q=1.35
IIIb p=12; q=1.70

The aryl polyglycol ethers of the formula III are likewise known.

The following products may be mentioned here as examples of block polymers of the formula IV:

| Total molecular weight | Molecular weight of the propylene oxide core | % content of ethylene oxide |
|---|---|---|
| 1,800–2,000 | 1,750 | 10 |
| 2,500–2,900 | 1,750 | 20 |
| 3,100–3,700 | 1,570 | 40 |
| 6,600–9,000 | 1,750 | 80 |
| 4,000–4,500 | 3,000 | 30 |
| 4,200–5,500 | 3,000 | 40 |
| 7,000–8,000 | 3,000 | 60 |

The compounds of the formula V are mixtures which differ on the one hand by the starting alcohol, for example butyl alcohol or alfols, and on the other hand by the different oxypropylene or oxyethylene content. Substances with the following composition may be mentioned:

α-butyl-omega-hydroxypoly-(oxypropylene) block polymer with a molecular weight of about 1,500, an ethylene oxide content of 54% and a total molecular weight of 3,500.

α-$C_{14}$-$C_{20}$-omega-hydroxypoly-(oxypropylene) block polymer with a molecular weight of about 1,200, an ethylene oxide content of 53% and a total molecular weight of 2,500–3,000.

Specific examples of the alkylaryl-sulfonic acids of the formula VI which may be mentioned are the following sulfonic acids:

4-(n- or iso-dodecyl)-benzene-sulfonic acid
4-(n-nonyl)-benzene-sulfonic acid

These acids are in the form of their salts with cations from group II or III of the periodic table. The calcium salt is preferred.

The compounds of the formula VII are based on the same sulfonic acids as those of the formula VI. Possible cations here are, for example, alkali metal or ammonium ions or quaternary ammonium ions which are derived from mono-, di- or trimethylamine, mono-, di- or triethylamine, monoisopropylamine, mono- or dibutylamine, 3-methoxypropylamine, mono-2-ethylhexylamine, dimethylaminopropylamine, mono-, di- or triethanolamine, 3-aminoprpanol, monomethylethanolamine, dimethylethanolamine, monoisopropanolamine, triisopropanolamine, cyclohexylamine, N,N-dimethylcyclohexylamine, morpholine, pyridine, quinoline, ethylenediamine, diethylenetriamine, pentaethylenehexamine or oxyethylated fatty amines. All these cations can also be present in the other anionic compounds of the formulae VII to XIII. Preferred cations here are in all cases alkali metal and ammonium ions.

The alkylaryl-sulfonic acid salts of the formulae VI and VII are known. They are in general used as 50–75% strength solutions in organic solvents, for example in n- or i-butanol, but they can in principle also be employed in higher concentrations or without a solvent.

Specific examples of compounds of the formula VIII which are mentioned are:

α-($C_{12}$-$C_{14}$)-alkyl-omega-hydroxypoly-(oxyethylene)-sulfate sodium salt with an oxyethylene content of 2 mol, α-($C_{12}$-$C_{14}$)-alkyl-omega-hydroxypoly-(oxyethylene)-sulfate sodium salt with an oxyethylene content of 3 mol.

An example of an alkylphenyl-omega-hydroxypoly-(oxyethylene)-sulfate salt of the formula IX which is mentioned is tributyl-phenyl-omega-hydroxypoly-(oxyethylene)-sulfate sodium salt with an oxyethylene content of 8 mol. These ether-sulfate salts of the formulae VIII and IX are also known. They are in general employed as 30–70% strength aqueous pastes.

Examples of alkyl-($C_8$-$C_{18}$)-sulfate or -sulfonate salts of the formula X which may be mentioned are the following compounds:

($C_{12}$-$C_{14}$)-alkyl-sulfate sodium salt
($C_{16}$-$C_{18}$)-alkyl-sulfate sodium salt
($C_{13}$-$C_{17}$)-alkyl-sulfonate sodium salt
($C_{14}$-$C_{16}$)-alkenyl-sulfonate sodium salt These compounds are in general employed as 20–80% strength aqueous pastes or solutions or as 100% pure powdered goods. The following compound may be mentioned as an example of a chloro-($C_4$-$C_{18}$)-alkyl-sulfonate as defined under formula X: chloro-alkyl-($C_{13}$-$C_{17}$)-sulfonate sodium salt. The chlorine content is in general 1.4–1.6 gram atoms of chlorine per mol of alkyl-sulfonate. These chloroalkylsulfonates are known and are in general used as a 50–70% strength solution in organic solvents, for example in n- or i-butanol, but they can on principle also be employed without a solvent.

An example of an alkylnaphthalenesulfonic acid salt of the formula XI which may be mentioned is mononenonylnaphthalenesulfonate sodium salt.

These alkylnaphthalenesulfonic acid salts are known. They are in general employed as 30–60% strength solutions in water/butanol or as 100% pure substances.

In formula XII, R preferably stands for a $C_{12}$-$C_{18}$-alkyl radical, $R_1$ stands for hydrogen, A stands for 1 and Ka stands for a mixed base of sodium hydroxide solution and triethanolamine. In the arylsulfonamidocarboxylic acid, R preferably stands for a benzene nucleus, $R_1$ stands for a methyl group, A stands for 5 and Ka stands for triethanolamine. These alkyl- or arylsulfonamidocarboxylic acids of the formula XII are known. They are in general employed as approximately 90–95% strength aqueous solutions.

In formula XIII, R preferably stands for an alkyl radical with 12 carbon atoms or an alkyl radical with 16 to 18 carbon atoms, $R_1$ stands for a methyl radical and Ka stands for sodium. The compounds of the formula XIII are known. The compounds wehre m=1 are employed as a 30% strength aqueous solution and the compounds where m=2 are employed as an approximately 33 or 64% strength powder.

Possible organic solvents which the oil-in-water emulsions according to the invention can optionally contain are all the customary organic solvents of low water-miscibility. Solvents which may be mentioned as preferred are aromatic hydrocarbons, such as xylene, toluene and dimethyl-naphthalene, mixtures of aromatics and furthermore chlorinated aromatic hydrocarbons, such as chlorobenzene; and in addition aliphatic hydrocarbons, such as benzine and petroleum ether, and moreover halogenated aliphatic hydroarbons, such as methylene chloride and chloroform, and furthermore cycloaliphatic hydrocarbons, such as cyclohexane, and in addition alcohols and ketones, such as n-butanol, i-butanol, n-hexanol, iso-hexanol, n-octanol, cyclohexanol, benzyl alcohol, di-n-butyl ketone and isophorone, cyclohexanone, acetophenone and furthermore ethers and esters, such as propylene glycol monomethyl ether, phthalates and proylene glycol monomethyl ether-acetate.

Possible solubilizers which the oil-in-water emulsions according to the invention can contain are all the customary solubilizing agents. Solubilizing agents which can preferably be used are alkylphenols, xylenols or cresols, which are condensed with 1 to 8 mol of ethylene oxide per mol. Examples which may be mentioned specifically in this connection are p-cresol which is condensed with 1 to 8 mol of ethylene oxide per mol, and xylenols which are condensed with 4 to 8 mol of ethylene oxide.

Possible additives which the oil-in-water emulsions according to the invention can optionally contain are preservatives, dyestuffs, buffers and low-temperature stabilizers. Examples of preservatives which may be mentioned are 2-hydroxybiphenyl and sorbic acid. Examples of dyestuffs which may be mentioned are azo dyestuffs and phthalocyanine dyestuffs. Buffer substances which may be mentioned here are sodium dihydrogen phosphate, ammonium acetate and diammonium phosphate. Examples of low-temperature stabilizers which may be mentioned are, preferably, glycerol, and also urea, ethylene glycol, propylene glycol, sugars and salts, such as ammonium sulfate and sodium oleate. These low-temperature stabilizers can be present in the emulsions according to the invention in amounts of 2 to 20, preferably 5 to 15% by weight. An example of a synergist which may be mentioned is 3,4-methylenedioxy-6-propyl-benzyl-n-butyl-diethylene glycol ether (piperonyl butoxide).

The percentage contents of the components contained in the oil-in-water microemulsions according to the invention can be varied within certain ranges. The content of active substance or active substances is in general between 0.1 and 80% by weight, preferably between 5 and 80% by weight. The content of emulsifier mixture is in general 1 to 30% by weight, preferably 3 to 16% by weight, it also being possible for the ratio between the emulsifiers to be varied within a certain range. In general, 1 t 1.3 parts of anionic emulsifier mixtures of the formulae VI–XIII are present per part of non-ionic emulsifiers of the formulae I–V.

Organic solvents of low water-miscibility and/or solubilizers can be present in amounts of 1 to 30% by weight, preferably 5 to 20% by weight. The percentage content of water in the microemulsions according to the invention is in each case calculated as the difference between 100% by weight and the sum of the percentage contents of the other components. The ratio of active substance(s), if appropriate mixed with organic solvents and/or solubilizers, to emulsifier mixture in the microemulsions according to the invention can be varied within a certain range. In general, 1 to 15 parts by weight, preferably 2 to 10 parts by weight of active substance(s), if appropriate mixed with organic solvents and/or solubilizers, are present per part of emulsifier mixture.

All those components which have already been mentioned as preferred in connection with the description of the oil-in-water microemulsions according to the invention can preferably be used in the preparation of the oil-in-water microemulsions according to the invention. If an active substance which is in the liquid state at temperatures up to 40° C. is used in the process according to the invention, it is in general not necessary to add an organic solvent of low water-miscibility and/or a solubilizer.

In contrast, if an active substance which is in the solid state at temperatures up to 40° C. is used in the process according to the invention, it is necessary to dissolve the active substance in question in an organic solvent of low water-miscibility and/or a solubilizer before the emulsification. The amount of organic solvent and/or solubilizer is chosen such that it is just sufficient to dissolve the solid substance. The reaction temperatures can be varied within a substantial range in the process according to the invention. The reaction is in general carried out at temperatures between 10° C. and 80° C., preferably between 20° C. and 60° C.

In carrying out the process according to the invention, a procedure is in general followed in which a homogeneous solution of one or more active substances, the emulsifiers, if appropriate organic solvents of low water-miscibility and/or a solubilizer and if appropriate additives, and this mixture is then added to water, if appropriate containing additives, with stirring. The amounts of the components are chosen here so that the components in the resulting oil-in-water microemulsion are present in the particular concentration desired. The sequence in which the components of the organic phase are brought together can be varied. The organic phase is advantageously added slowly to the aqueous phase with uniform stirring with customary stirring units. A finely divided microemulsion in which the droplets have a diameter between 0.05 $\mu$m and 1 $\mu$m or smaller is thereby formed. After-treatment with homogenizers of the oil-in-water microemulsion formed is not necessary, but can be carried out if desired.

The oil-in-water microemulsions according to the invention can be applied either inthe form as prepared or after prior dilution. The amount applied depends here on the concentration of the active substances in the oil-in-water microemulsion and on the particular indication.

The oil-in-water microemulsions according to the invention are used by customary methods, that is to say, for example, by spraying, atomizing or pouring.

The preparation of the oil-in-water microemulsions according to the invention is evident from the following examples.

PREPARATION EXAMPLES

An emulsifier mixture is added at temperatures between 20° C. and 40° C., with stirring, to the active substances or active substance solutions to be formulated. The homogeneous solution thereby formed is added to water in the course of 2–4 minutes with gentle stirring (blade stirrer). When the addition has ended, the mixture is subsequently stirred for a further 5 minutes. A slightly colored, slightly viscous oil-in-water microemulsion which shows no chemical or physical changes on prolonged storage at between −10° C. and 54° C. is formed. If necessary, stabilizers, preservatives, low-temperature stabilizers and dyestuffs are added to the water needed to form the microemulsion. This is illustrated by the following examples:

Preparation Examples

| | component | | | | | | | | | |
|---|---|---|---|---|---|---|---|---|---|---|
| | 1 % | 2 % | 3 % | 4 % | 5 % | 6 % | 7 % | 8 % | 9 % | 10 % |
| 0,0-dimethyl 0-(4-methylmercapto-3-methyl-phenyl) thionophosphate 100% pure = Lebaycid | 50 | 50 | 50 | 50 | 50 | 25 | 25 | 50 | 50 | 50 |
| tris-(α-methyl-benzyl)-phenyl polyglycol ether with on average 22 mol of ethylene oxide units | 8.5 | 8.6 | 9.7 | 10.2 | 18 | 7.5 | 8.1 | 8.7 | 8.5 | 7.5 |
| n-dodecylbenzenesulfonic acid calcium salt, 70% strength in isobutanol | 5.9 | 5.8 | 7.9 | 7.4 | 11.9 | 6.9 | 6.3 | 6.7 | 6.9 | 6.9 |
| water | 34 | 24 | 30 | 20 | 20 | 59 | 49 | 34 | 24 | 24 |
| n-dodecylbenzenesulfonic acid sodium salt 100% pure | 1.6 | 1.6 | 2.4 | 2.4 | 0.1 | 1.6 | | | | |
| glycerol | | 10 | | 10 | | | 10 | | 10 | 10 |
| α-alkyl($C_{12}$—$C_{14}$)-omega hydroxypoly-(oxyethylene)-sulfate sodium salt with an oxyethylene content of about 2 mol 100% pure | | | | | | | | 0.6 | 0.6 | |
| tributyl-phenyl-omega-hydropoly-(oxyethylene)-sulfate sodium salt with an α-ethylene content of on average 8 mol 100% pure | | | | | | | | | | 1.6 |
| temperature stability °C. | 22 to 54 | −5 to 54 | 22 to 54 | −5 to 54 | −5 to 54 | 22 to 54 | 10 to 54 | 22 to 50 | 10 to 22 | 10 to 45 |

Preparation Examples

| | component | | |
|---|---|---|---|
| | 11 % | 12 % | 13 % |
| 0,0-dimethyl 0-(4-methylmercapto-3-methyl-phenyl) thionophosphate 100% pure | 50 | 50 | 50 |
| tris-(α-methyl-benzyl)-phenyl polyglycol ether with on average 22 mol of oxyethylene units | 8.6 | 9.4 | 9.0 |
| n-dodecylbenzenesulfonic acid calcium salt, 70% strength in isobutanol | 6.8 | 6.2 | 6.6 |
| water | 34 | 34 | 34 |
| alkyl-($C_{12}$—$C_{14}$)-sulfate sodium salt 100% pure | 0.6 | | |
| alkyl-($C_{16}$—$C_{18}$)-sulfate sodium salt 100% pure | | | |
| alkyl-($C_{13}$—$C_{17}$)-sulfonate sodium salt 100% pure | | 0.4 | |
| alkenyl-($C_{14}$—$C_{16}$)-sulfonate sodium salt 100% pure | | | 0.4 |
| temperature stability °C. | 22 to 50 | 22 to 45 | 22 to 45 |

Preparation Examples

| | component | |
|---|---|---|
| | 14 % | 15 % |
| 0,0-dimethyl 0-(4-methylmercapto-3-methyl-phenyl) thionophosphate 100% pure | 50 | 50 |
| tris-(α-methyl-benzyl)-phenyl polyglycol ether with on average 22 mol of oxyethylene units | 8.6 | 7.9 |
| n-dodecylbenzenesulfonic acid calcium salt, 70% strength in isobutanol | 5.8 | 6.5 |
| water | 34 | 34 |
| chloro-alkyl-($C_{15}$—$C_{17}$)-sulfonate sodium salt 100% pure | 1.6 | |
| mononoylnaphthalensulfonate sodium salt 100% pure | | 1.6 |
| alkyl-($C_{12}$—$C_{18}$)-sulfonamidoacetic acid sodium and tri-ethanolamine mixed base 100% pure | | |
| temperature stability °C. | 35 to 54 | 10 to 45 |

Preparation Examples

| | component 16 % |
|---|---|
| 0,0-dimethyl 0-(4-methylmercapto-3-methyl-phenyl) thionophosphate 100% pure | 25 |
| tris-(α-methyl-benzyl)-phenyl polyglycol ether with on average 22 mol of oxyethylene units | 7.2 |
| n-dodecylbenzenesulfonic acid calcium salt, 70% strength in isobutanol | 4.8 |
| water | 62 |
| N-methyl-arylsulfonyl ε-aminocaproic acid triethanolammonium salt 100% pure | 1.0 |
| N-methyl-lauroylsarcoside sodium salt 100% pure | |
| N-methyl-oleoylmethyltauride sodium salt 100% pure | |
| temperature stability °C. | 22 to 50 |

Preparation Examples

| | component | | | | |
|---|---|---|---|---|---|
| | 17 % | 18 % | 19 % | 20 % | 21 % |
| butylglycol 2-(4-chloro-0-tolyloxy)-propionate 100% pure = CMPP butylglycol ester | 25 | 50 | | | |
| butylglycol (4-chloro-0-tolyloxy)-acetate 100% pure = MPCA butylglycol ester | | | 25 | 50 | |

-continued

| | | | | | |
|---|---|---|---|---|---|
| ethyl 2-diethoxythiophosphoryloxy-5-methylpyrazolo-[1,5-a]-pyrimidine-6-carboxylate 60% strength in xylene | | | | | 50 |
| tris-(α-methyl-benzyl)-phenyl polyglycol ether with on average 22 mol of oxyethylene units | 8.6 | 8.6 | 8.6 | 8.6 | 8.6 |
| n-dodecylbenzenesulfonic acid calcium salt, 70% strength in isobutanol | 5.8 | 5.8 | 5.8 | 5.8 | 5.8 |
| water | 49 | 24 | 49 | 24 | 24 |
| n-dodecylbenzenesulfonic acid sodium salt 100% pure | 1.6 | 1.6 | 1.6 | 1.6 | 1.6 |
| glycerol | 10 | 10 | 10 | 10 | 10 |
| temperature stability °C. | −10 to 40 | −10 to 50 | −10 to 40 | −10 to 50 | −10 to 50 |

Preparation Examples

| component | 22 % | 23 % | 24 % | 25 % |
|---|---|---|---|---|
| α,α,α-trifluoro-2,6-dinitro-N,N-dipropyl-p-toluidine 40% strength in Solvesso 150 | 25 | | | |
| ethyl ± 2-[4-(6-chlorobenzoxyzol-2-yloxy)-phenoxy]-propionate 40% strength in cyclohexane | | 40 | | |
| 7-chlorobicyclo-[3.2.0]-hepta-2,6-dien-6-yl dimethyl phosphate in Example 24 100% pure in Example 25 50% strength in xylene | | | 50 | 50 |
| tris-(α-methyl-benzyl)-phenyl polyglycol ether with on average 22 mol of oxyethylene units | 8.6 | 8.6 | 8.6 | 8.6 |
| n-dodecylbenzenesulfonic acid calcium salt, 70% strength in isobutanol | 5.8 | 5.8 | 5.8 | 5.8 |
| water | 49 | 34 | 24 | 24 |
| n-dodecylbenzenesulfonic acid sodium salt 100% pure | 1.6 | 1.6 | 1.6 | 1.6 |
| glycerol | 10 | 10 | 10 | 10 |
| temperature stability °C. | −10 to 50 | 20 to 50 | −10 to 50 | −10 to 50 |

Preparation Examples

| component | 26 % | 27 % | 28 % | 29 % | 30 % | 31 % | 32 % |
|---|---|---|---|---|---|---|---|
| 0,0-diethyl 0-1-phenyl-1,2,4-triazol-3-yl phosphorothioate in Example 26 + 27 70% strength in xylene in Example 28 50% strength in xylene | 57.2 | 35.7 | 50 | | | | |
| methyl 2-[4-(2,4-dichlorophenoxy)-phenoxy] propionate in Example 29 20% strength in xylene in Example 30 40% strength in xylene in Example 31 25% strength in xylene | | | | 50 | 50 | 39 | |
| xylene | | | | | | | 25 |
| tris-(α-methyl-benzyl)-phenyl polyglycol ether with on average 22 mol of oxyethylene units | 8.6 | 8.6 | 8.6 | 8.6 | 8.6 | 8.6 | 8.6 |
| n-dodecylbenzenesulfonic acid calcium salt, 70% strength in isobutanol | 5.8 | 5.8 | 5.8 | 5.8 | 5.8 | 5.8 | 5.8 |
| water | 16.8 | 38.3 | 24 | 24 | 24 | 35 | 49 |
| n-dodecylbenzenesulfonic acid sodium salt 100% pure | 1.6 | 1.6 | 1.6 | 1.6 | 1.6 | 1.6 | 1.6 |
| glycerol | 10 | 10 | 10 | 10 | 10 | 10 | 10 |
| temperature stability °C. | −10 to 10 | −10 to 30 | −10 to 40 | −10 to 40 | −10 to 40 | −10 to 50 | −10 to 60 |

Preparation Examples

| component | 33 % | 34 % | 35 % | 36 % |
|---|---|---|---|---|
| Solvesso 150 | 50 | 25 | | |
| isophorone | | | 25 | |
| cyclohexane | | | | 25 |
| tris-(α-methyl-benzyl)-phenyl polyglycol ether with on average 22 mol of oxyethylene units | 8.6 | 8.6 | 8.6 | 8.6 |
| n-dodecylbenzenesulfonic acid calcium salt, 70% strength in isobutanol | 5.8 | 5.8 | 5.8 | 5.8 |
| water | 24 | 49 | 49 | 49 |
| n-dodecylbenzenesulfonic acid sodium salt 100% pure | 1.6 | 1.6 | 1.6 | 1.6 |
| glycerol | 10 | 10 | 10 | 10 |
| temperature stability °C. | −10 to 50 | −10 to 50 | −10 to 50 | −10 to 50 |

Preparation Examples

| component | 37 % | 38 % | 39 % | 40 % |
|---|---|---|---|---|
| 0,0-dimethyl 0-(4-methylmercapto-3-methylphenyl) thiophosphate | 50.0 | 50.0 | 50.0 | 50.0 |
| tris-(α-methyl-p-methylbenzyl)-phenyl polyglycol ether with on average 17 mol of oxyethylene units | 5.1 | 5.1 | 5.1 | 5.1 |
| tris-(α-methyl-p-methylbenzyl)-phenyl polyglycol ether with on average 27 mol of oxyethylene units | 2.5 | 2.5 | 2.5 | 2.5 |
| n-dodecylbenzenesulfonic acid calcium salt, 70% strength in n-butanol | 4.9 | 4.9 | 4.9 | 4.9 |

-continued

| | | | | |
|---|---|---|---|---|
| n-dodecylbenzenesulfonic acid Na salt | 0.5 | 0.7 | 0.25 | 0.4 |
| polyglycol ether with an average molecular weight of 400 | | | 5.0 | 5.0 |
| water | 37.0 | 36.8 | 32.25 | 32.1 |
| temperature stability °C. | 22 to 42 | 25 to 45 | 3 to 38 | 18 to 38 |

Preparation Examples

| | component | | | | |
|---|---|---|---|---|---|
| | 41 % | 42 % | 43 % | 44 % | 45 % |
| O-ethyl O-(3-methyl-4-methylthio-phenyl)-isopropylamido phosphate | 28.0 | 28.0 | 28.0 | 28.0 | 28.0 |
| n-butanol | 20.0 | 20.0 | 20.0 | 20.0 | 20.0 |
| tris-(α-methyl-p-methylbenzyl)-phenyl polyglycol ether with on average 17 mol of oxyethylene units | 15.3 | 15.3 | 15.5 | | 4.0 |
| tris-(α-methyl-p-methylbenzyl)-phenyl polyglycol ether with on average 27 mol of oxyethylene units | | | | 15.3 | 11.0 |
| N-dodecylbenzenesulfonic acid calcium salt, 70% strength in n-butanol | 1.6 | 1.7 | | 1.7 | |
| n-dodecylbenzenesulfonic acid Na salt | 0.1 | 1.0 | 1.5 | 1.0 | 1.5 |
| water | 35.0 | 34.0 | 35.0 | 34.0 | 35.5 |
| temperature stability °C. | 0 to 25 | 0 to 32 | 0 to 35 | 0 to 42 | 0 to 42 |

EXAMPLE 46

28.1 parts by weight of endosulfan (95.5% pure) are dissolved completely in 19.5 parts by weight of a $C_9$, $C_{10}$, $C_{11}$-aromatic mixture and 13 parts by weight of cyclohexanone, with stirring. 5 parts by weight of calcium phenylsulfonate, 10 parts by weight of tristyrylphenol +20 mol of ethylene oxide and 4 parts by weight of $C_{13}$-$C_{17}$-sec.-alkanesulfonate are also dissolved in 20.4 parts by weight of water. This solution is slowly added to the first solution, with stirring, and the mixture is then subsequently stirred for 1 hour. A transparent emulsion which is stable in respect of the active substance content and technological properties on storage at 54° C. for 14 days is obtained. The low-temperature stability is 14 days at 0° C. At −10° C., traces of crystals may occur after about 11 days.

We claim:

1. An oil-in-water emulsion which contains 0.01–80% by weight of at least one active substance having a maximum solubility of 0.5% by weight in water at 20° C. and
1 to 30% by weight of an emulsifier mixture comprising
  (a) 30–80% by weight of one or more compounds of the formulae I–IV

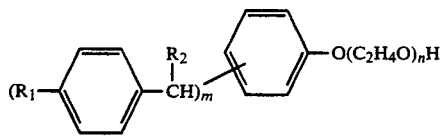
I in which
R₁ denotes hydrogen or $C_1$-$C_{16}$-alkyl,
R₂ denotes hydrogen or methyl,
m denotes a number from 1 to 4 and
n denotes a number from 10 to 60,

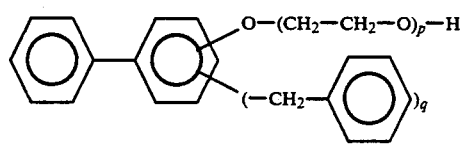
II in which
p denotes a number from 5–40 and
q denotes a number from 1–3,

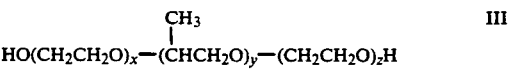
III in which x, y and z represent numbers which are chosen so that the molecular weight is 1,800 to 16,000 in total,

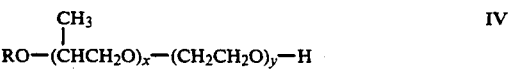
IV in which R denotes $C_3$-$C_{18}$-alkyl and x and y represent numbers which are chosen so that the molecular weight is 2,000 to 7,000 in total,
(b) 20–50% by weight of a compound of the formula VI

VI in which $R_1$ denotes $C_4$-$C_{35}$-alkyl and Me denotes a metal cation from group II or III of the periodic table, and
(c) 0.1–2.0% by weight of one or more compounds of the formulae VII–XI

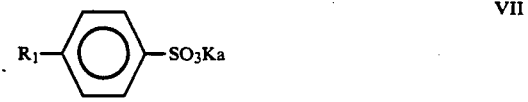
VII in which $R_1$ has the same meaning as for formula VI and Ka denotes alkali metal and ammonium ions,

R—O—(CH₂CH₂O)ₓSO₃Ka     VIII in which R denotes $C_6$-$C_{18}$-alkyl, x denotes a number from 2 to 8 and Ka has the meaning given in the case of formula VII,

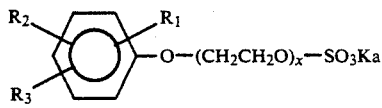

in which $R_1$, $R_2$ and $R_3$ denote hydrogen or $C_1$–$C_{20}$-alkyl, x denotes a number from 5 to 50 and Ka has the meaning given in the case of formula VII,

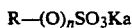

in which R denotes $C_8$–$C_{18}$-alkyl or $C_8$–$C_{18}$-alkenyl or, in the case where $n=0$, also denotes $C_4$–$C_{18}$-chloroalkyl, n denotes 0 or 1 and Ka has the meaning given in the case of formula VII,

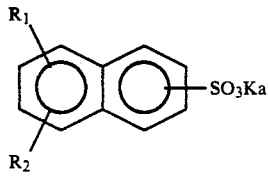

in which $R_1$ denotes $C_3$–$C_{13}$-alkyl and $R_2$ denotes hydrogen, or $R_1$ and $R_2$ denote $C_3$–$C_{13}$-alkyl and Ka has the meaning given in the case of formula VII, and water, and
up to 30% by weight of at least one organic solvent of low water-miscibility or of one stabilizer or of a mixture thereof, and
up to 15% by weight of additives, the sum of the components in each case being 100% by weight.

2. An oil-in-water emulsion as claimed in claim 1, wherein the emulsifier mixture consists essentially of:
  (a) 50–60% by weight of one or more compounds of said formulae I–IV,
  (b) 30–40% by weight of a compound of said formula VI, and
  (c) 0.1–10% by weight of one or more compounds of said formulae VII–XI.

3. An oil-in-water emulsion as claimed in claim 1, wherein the emulsion contains:
  1 to 30% by weight of at least one said organic solvent of low miscibility or of one said stabilizer or of a said mixture thereof, and
  0.1 to 15% by weight of said additives.

4. An oil-in-water emulsion as claimed in claim 1, which contains 2–20% by weight of glycerol as a stabilizer.

5. An oil-in-water emulsion as claimed in claim 4, wherein said amount of glycerol is 5–15% by weight.

6. An oil-in-water emulsion as claimed in claim 1, which consists essentially of:
  5 to 80% by weight of said active substance,
  1 to 30% by weight of said emulsifier mixture, water, and
  no more than 20% by weight of said organic solvent or stabilizer or mixture thereof.

7. An oil-in-water emulsion which contains 0.01–80% by weight of at least one active substance having a maximum solubility of 0.5% by weight in water at 20° C. and
1 to 30% by weight of an emulsifier mixture comprising (a) 30–80% by weight of one or more compounds of the formulae I–IV

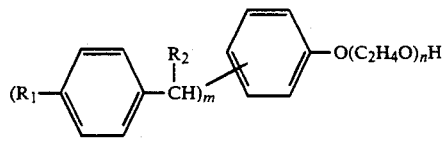

in which
$R_1$ denotes hydrogen or $C_1$–$C_{16}$-alkyl,
$R_2$ denotes hydrogen or methyl,
m denotes a number from 1 to 4 and
n denotes a number from 10 to 60,

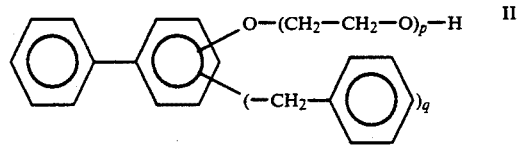

in which
p denotes a number from 5–40 and
q denotes a number from 1–3,

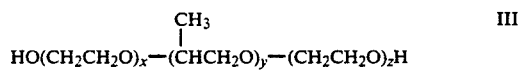

in which x, y and z represent numbers which are chosen so that the molecular weight is 1,800 to 16,000 in total,

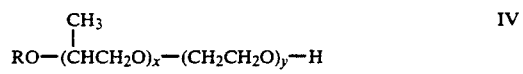

in which R denotes $C_3$–$C_{18}$-alkyl and x and y represent numbers which are chosen so that the molecular weight is 2,000 to 7,000 in total,
(b) 20–50% by weight of a compound of the formula VI

in which $R_1$ denotes $C_4$–$C_{35}$-alkyl and Me denotes a metal cation from group II or III of the periodic table, and
(c) 0.1–20by weight of one or more compounds of the formulae VII–XI

in which $R_1$ has the same meaning as for formula VI and Ka denotes a cation selected from the group consisting of alkali metal ions, ammonium ions and ions, which are derived from mono-, di- or trimethylamine, mono-, di- or triethylamine, monoisopropylamine, mono- or dibutylamine, 3-methoxypropylamine, mono-2-ethyl-hexylamine, di-methylaminopropylamine, mono-, di- or triethanolamine, 3-aminopropanol, monomethylethanolamine, dimethylethanolamine, monoisopropanolamine, triisopropanolamine, cyclohexylamine, N,N-dimethylcyclohexylamine, morpholine, pyridine, quinoline, ethylenediamine, diethylenetriamine, pentaethylenehexamine, or oxyethylated fatty amines, $$R-O-(CH_2CH_2O)_x-SO_3Ka \qquad \text{VIII}$$

in which R denotes $C_6-C_{18}$-alkyl, x denotes a number from 2 to 8 and Ka has the meaning given in the case of formula VII,

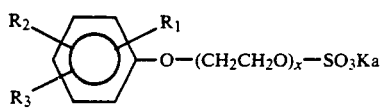

in which $R_1$, $R_2$ and $R_3$ denote hydrogen or $C_1-C_{20}$-alkyl, x denotes a number from 5 to 50 and Ka has the meaning given in the case of formula VII, $$R-(O)_nSO_3Ka \qquad \text{X}$$

in which R denotes $C_8-C_{18}$-alkyl or $C_8-C_{18}$-alkenyl or, in the case where n=O, also denotes $C_4-C_{18}$-chloroalkyl, n denotes 0 or 1 and Ka has the meaning given in the case of formula VII,

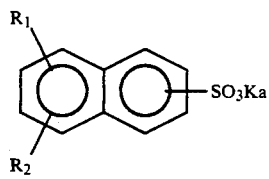

in which $R_1$ denotes $C_3-C_{13}$-alkyl and $R_2$ denotes hydrogen, or $R_1$ and $R_2$ denote $C_3-C_{13}$-alkyl and Ka has the meaning given in the case of formula VII, and water, and up to 30% by weight of at least one organic solvent of low water-miscibility or of one stabilizer or of a mixture thereof, and up to 15% by weight of additives, the sum of the components in each case being 100% by weight.

8. An agrochemical composition consisting essentially of:

0.01 to 80% by weight of an agrochemical active substance, 1 to 30% by weight of an emulsifier mixture of claim 5, water, up to 30% by weight of at least one organic solvent of low water-miscibility or of one stabilizer or of a mixture thereof, and up to 15% by weight of additives, the sum of the components in each case being 100% by weight.

9. An agrochemical composition as claimed in claim 8, wherein the amount of said organic solvent or solvents is no more than 20% by weight of said composition, and the amount of agrochemical active substance is 5 to 80% by weight of said composition.

10. A method of using the composition of claim 8 comprising the step of spraying the composition onto plants for plant protection.

* * * * *